United States Patent [19]
Bhatta

[11] Patent Number: 5,462,753
[45] Date of Patent: Oct. 31, 1995

[54] TREATMENT OF SYMPTOMATIC BENIGN PROSTATIC HYPERPLASIA

[76] Inventor: Krishna M. Bhatta, 60 High St., Skowhegan, Me. 04976

[21] Appl. No.: 56,130

[22] Filed: Apr. 30, 1993

[51] Int. Cl.[6] ................................................ A61K 33/36
[52] U.S. Cl. ............................................................ 424/670
[58] Field of Search ............................................... 424/670

[56] References Cited

U.S. PATENT DOCUMENTS 4,946,688  8/1990  Fahim ..................................... 424/643
5,102,912  4/1992  Streber .................................... 514/529

*Primary Examiner*—Jerome D. Goldberg
*Attorney, Agent, or Firm*—Hayes, Soloway, Hennessey, Grossman & Hage

[57] ABSTRACT

Use of potassium iodide, administered orally, in an average daily dosage of 0.10 to 0.40 milligrams for the treatment of symptomatic Benign Prostatic Hyperplasia. The potassium iodide preferably is used in the form of a saturated aqueous solution of potassium iodide.

2 Claims, No Drawings

TREATMENT OF SYMPTOMATIC BENIGN PROSTATIC HYPERPLASIA

BACKGROUND OF THE INVENTION

Benign Prostatic Hyperplasia (BPH) is common in adult males. Mankind is not unique in this regard and other animals with a compact or solid prostate, such as dogs, suffer comparably. BPH is particularly common in men over age 50. Patients with symptoms traditionally have been treated with transurethral resection of the prostate (TURP), a surgical technique that effectively reduces bladder outlet obstruction. TURP works best for those who need it most and it works poorest for those who need it least. Other modalities for the treatment of patients with moderate or severe symptoms of BPH and/or those who are not suitable or do not elect to have a surgery also have been proposed, and data is being evaluated to determine the efficacy of treating symptomatic BPH with modalities such as a balloon dilatation, prostate hyperthermia, laser coagulation and prostatic stents. Recently, Doll et al reported in J. Urol., 147, 1566–1573, 1992, that 96% of severely symptomatic men experience improvement after transurethral resection of prostate, while only 18% of mildly symptomatic men improve.

Recently, non-surgical treatment of BPH has been suggested as an alternative, including androgen suppression using alpha 1 blockers and/or 5 alpha-reductase inhibitor (finasteride). The maximum effects of finasteride on reducing prostatic volume occurs after three months of oral therapy. Most patients experience improvements in their symptoms and flow rates. However, serum DHT levels return to baseline within two weeks following discontinuation of the treatment. Most patients have to be on this for a long term to maintain the benefits. Moreover, it is fairly expensive medication at present. Similarly, beneficial effects of alpha 1 selective blockers take approximately two months to peak and have to be maintained on a long term basis for continued benefits in their symptomatology with BPH.

SUMMARY OF THE INVENTION

The present invention is based on the discovery that potassium iodide can be used successfully for the treatment of symptomatic Benign Prostatic Hyperplasia (BPH) by administering an effective course of potassium iodide administered orally.

The pharmaceutical preparation comprising potassium iodide in accordance with the present invention can be administered in a daily dose which averages about 50 to about 1000 milligrams of potassium iodide, preferably about 300 to about 600 milligrams of potassium iodide per daily dose. Preferably the potassium iodide is taken orally, in liquid drink, twice daily for five to ten days, preferably ten days. Alternatively, the potassium iodide may be taken every other day at twice the aforesaid daily dose. Alternatively, the potassium iodide may be administered carried in gelatin capsules or the like, or in suspension or solution in a palatable carrier that masks the taste.

Potassium iodide oral solution is available from Upsher-Smith Laboratories, Inc., Minneapolis, Minn. under the trademark SSKI™. According to the manufacturer, SSKI™ potassium iodide oral solution is a saturated solution of potassium iodide containing one gram of potassium iodide per milliliter. The potassium iodide oral solution should be diluted, for example, and taken with a glass of juice or milk.

Administration of potassium iodide in accordance with the present invention has been observed to have a remarkable effect of improvements in uroflow and relief from symptoms of BPH.

The methods of the present invention will now be described by way of example, with reference to particular patients treated during trials of the invention.

Six patients were evaluated in a preliminary evaluation study. They all had a AUA symptom score recorded before and after the treatment with potassium iodide. A uroflow was obtained in all patients before and after the treatment. Two of the six patients had previous TURPs and had continued to experience moderate to severe prostatism symptoms. Results were evaluated based on improvements in AUA symptom scores, quality of life questions and improvements in their uroflow results.

RESULTS

Of the six patients three had BPH and two had transurethral resection of prostate in the past and still had significant prostatism as determined by AUA symptom scores. Table I shows their diagnosis and AUA symptom scores pre and post treatment.

Five of the six patients received the medication (10 drops-0.3 ml. of potassium iodide saturated solution-300 milligrams of potassium iodide-twice daily, taken orally with juice or milk) for ten days. One patient discontinued treatment on the fourth day because he developed gastric irritation, a severe metallic taste and a rash over his body. However, even he did notice a significant reduction in his symptoms (AUA score dropped from 11 to 4). One other patient reported a metallic taste for two to three days after stopping the medicine, but this reportedly disappeared spontaneously in 2–3 days.

Improvements in symptom scores of more than ten points occurred in all patients except one patient on whom cystoscopy done later revealed a diagnosis of contracture of bladder neck. His AUA symptom scores were 20 and 16 respectively before and after treatment. One other patient whose AUA symptom scored dropped to 18 from 28 and also noted improvement in flow still was not happy with his state of life and opted to have a TURP performed.

A six month follow-up is available in one patient. He developed recurrence of symptoms after three months. He took another ten day course and has been fine since then. In most cases an improvement was obvious by third or fourth day and peaked between the seventh and tenth day.

The four patients who noticed marked improvement in their symptoms were all considering a TURP for their symptomatic BPH. They were happy with the results. One patient opted for a TURP because he still was having moderate symptoms (AUA symptom score dropped to 18 from 28) and another is considering surgical intervention because he did not have a significant relief symptoms (AUA score dropped to 16 down from 20).

The improvements in symptoms in this study occurred within seven to ten days of treatment with potassium iodide oral solution. The improvements were quite significant as noted in Table I.

The mechanism whereby potassium iodide improvements symptoms in BPH is not understood at the present time. Potassium iodide is known to reduce vascularity in thyroid glands; however, whether or not it has any effect on vascular supply of prostate is not known.

TABLE 1

| CASE # | SYMPTOM SCORE PRE-Rx | SYMPTOM SCORE POST-Rx | % INCREASE |
|---|---|---|---|
| 1 | 17 | 2 | 88 |
| 2 | 29 | 8 | 72 |
| 3 | 19 | 4 | 79 |
| 4 | 20 | 16 | 25 |
| 5 | 11 | 5 | 64 |
| 6 | 28 | 18 | 86 |

CONCLUSION

Potassium iodide was found to reduce AUA symptom scores in patients with symptomatic BPH.

While the invention has been described in connection with the preferred embodiment, various modifications may be made without departing from the spirit and scope thereof. It is intended that all such modifications which fall within the scope and spirit of the appended claims be embraced thereby.

I claim:

1. A method of treating symptomatic benign prostatic hyperplasia in a human male which comprises administering orally to the male an average daily dosage of 50 to 1000 milligrams of potassium iodide for a period of from five to ten days.

2. A method according to claim 1, wherein said potassium iodide is administered in an average daily dosage of 300 to 600 milligrams for a period of ten days.

* * * * *